(12) United States Patent
Anazawa et al.

(10) Patent No.: US 6,585,954 B1
(45) Date of Patent: Jul. 1, 2003

(54) METHOD FOR SEARCHING STEROID SULFATASE INHIBITORS

(75) Inventors: Hideharu Anazawa, Tokyo (JP); Yoko Kato, Machida (JP); Hiroyuki Ishida, Shizuoka (JP); Taisuke Nakata, Mishima (JP); Shiro Akinaga, Shizuoka (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/646,683

(22) PCT Filed: Mar. 26, 1999

(86) PCT No.: PCT/JP99/01546

§ 371 (c)(1),
(2), (4) Date: Sep. 20, 2000

(87) PCT Pub. No.: WO99/50453

PCT Pub. Date: Oct. 7, 1999

(30) Foreign Application Priority Data

Mar. 26, 1998 (JP) ............................................. 10/078859

(51) Int. Cl.$^7$ ............................. C12Q 1/34; C12Q 1/68; C12N 5/10; C12N 15/55
(52) U.S. Cl. ............................. 424/9.2; 435/6; 435/18; 435/29; 435/325
(58) Field of Search ............................. 424/9.2; 435/6, 435/29, 69.1, 325, 243; 800/3

(56) References Cited

U.S. PATENT DOCUMENTS 5,837,853 A  11/1998  Takashima et al. ......... 536/24.5

FOREIGN PATENT DOCUMENTS

| | | |
|---|---|---|
| JP | 4-502261 | 4/1992 |
| WO | WO 91/02085 | 2/1991 |
| WO | WO 91/05794 | 5/1991 |
| WO | WO 93/05396 | 3/1993 |
| WO | WO 94/09116 | 4/1994 |

OTHER PUBLICATIONS

Fetal Bovine Serum. Datasheet [online]. Atlanta Biologicals [retrieved on 2001–10–11]. Retrieved from the Internet: URL:www.atlantabio.com/fetal_bovine_serum.htm.*

T Yamamoto et al. The inhibitory effecr of medroxyprogesterone acetate on steroid sulfatase in human uterine endometrial cancer cells endocine–related cancer 1996 337–340.*
Zhou et al, Cancer Research, vol. 50 (1990), pp. 6949–6954.
Santner et al, J. Steroid Biochem. Molec. Biol., vol. 44, No. 4 (1993), pp. 611–616.
Yue, et al, Cancer Research, vol. 55 (1995), pp. 3073–3077.
Santner et al, Journal of Clinical Endocrinology and Metabolism, vol. 59, No. 1 (1984), pp. 29–33.
Santen et al, Ann. NY Acad. Sci., vol. 464 (1986), pp. 126–137.
Pasqualini et al, J. Steroid Biochem. Molec. Biol., vol. 34, Nos 1–6, (1989), pp. 155–163.
Li et al, Steroids, vol. 58 (1993), pp. 106–111.
Purohit et al, J. Steroid Biochem. Molec. Biol., vol. 48, No. 5/6 (1994), pp. 523–527.
Li et al, J. Steroid Biochem. Molec. Biol., vol. 59, No. 1 (1996), pp. 41–48.
Anderson et al, Biochemistry, vol. 36 (1997), pp. 2586–2594.
Selcer et al, J. Steroid Biochem. Molec. Biol., vol. 59, No. 1 (1996), pp. 83–91.
Selcer et al, Cancer Research, vol. 57 (1997), pp. 702–707.
Stein et al, The Journal of Biological Chemistry, vol. 264, No. 23 (1989), pp. 13865–13872.
Purohit et al, J. Steroid Biochem. Molec. Biol., vol. 50, No. 1, 2 (1994), pp. 101–104.
Salido et al, Nature Genetics, vol. 13 (1996), pp. 83–86.
Iacobelli et al "Effects of the Antiestroger, Tamoxifen, on Protein Synthesis and Cell Division of Human Breast Cancer Cells in vitro" in *The Role of Tamoxifen in Breast Cancer*, edited by S. Iacobelli, M. Lippman and G. Robvstellidella Cuna, Raven Press 1982.

* cited by examiner

Primary Examiner—Remy Yucel
Assistant Examiner—Bronwen M. Loeb
(74) Attorney, Agent, or Firm—Fitzpatrick, Cella, Harper & Scinto

(57) ABSTRACT

The present invention provides a method of efficiently screening for steroid sulfatase activity-inhibiting compounds which are useful for the treatment of hormone-dependent diseases such as breast cancer, etc. by causing a test compound to act on cells carrying an introduced steroid sulfatase gene and estimating the inhibiting activity of the compound on the growth of the cells.

6 Claims, 4 Drawing Sheets

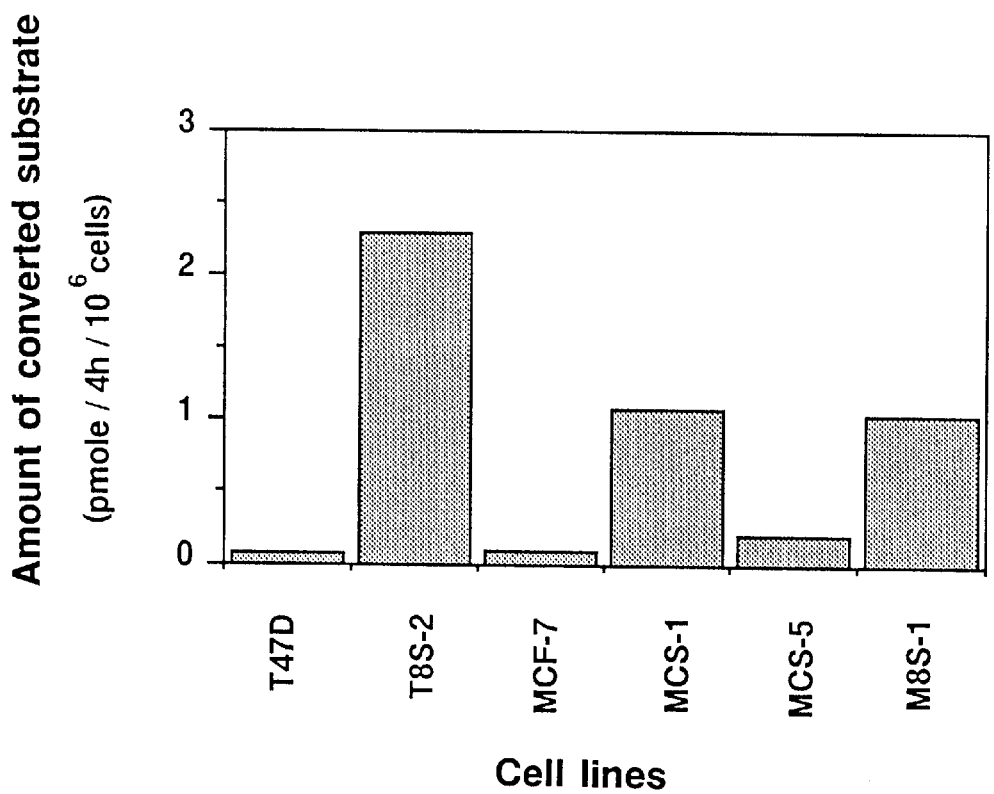
Fig. 1   Steroid sulfatase activity of transformed cells
T47D, MCF-7: parent cell lines
T8S-2, MCS-1, MCS-5, M8S-1: transformed cell lines

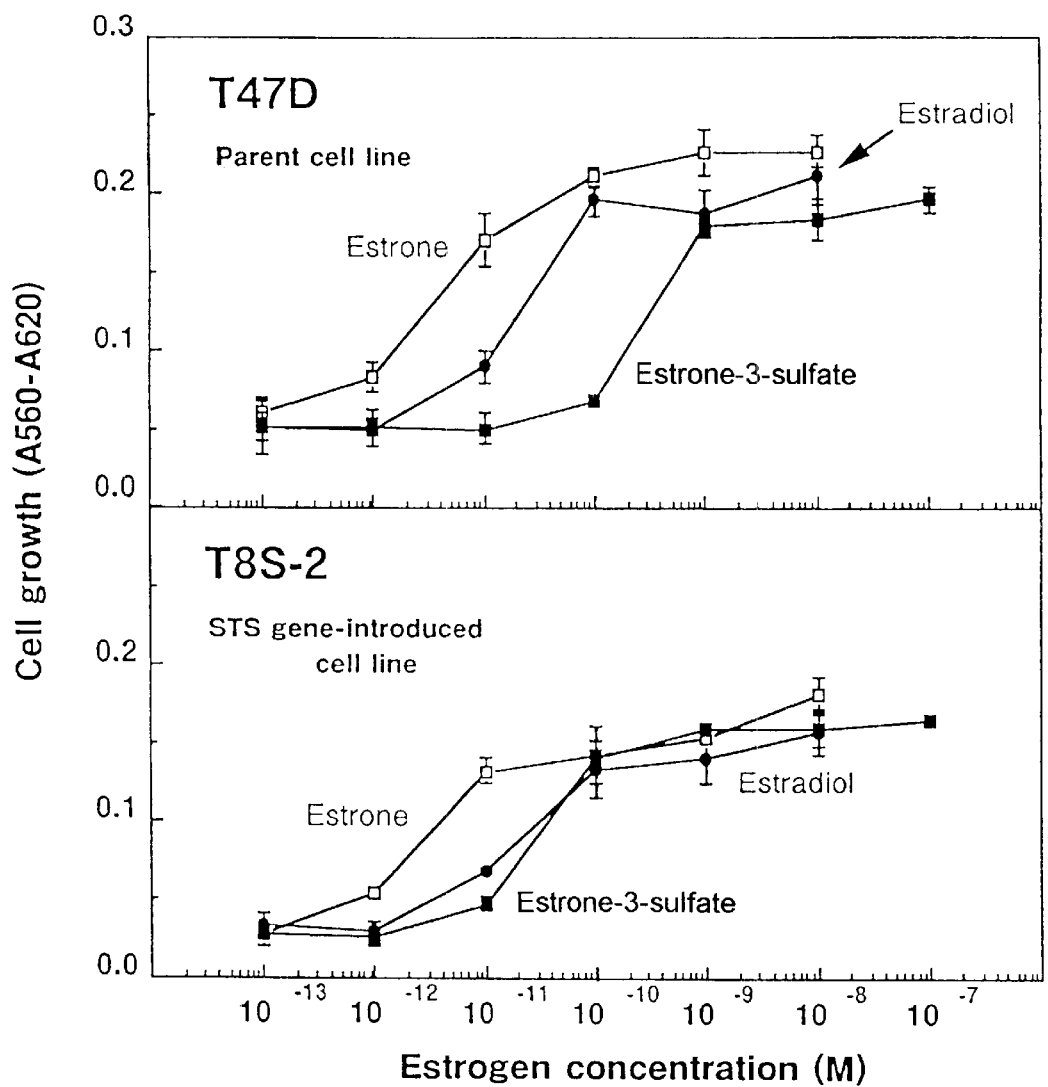
Fig. 2 Change in the dependence of growth of transformed cells on estrogen compounds
T47D: parent cell line
T8S-2: transformed cell line

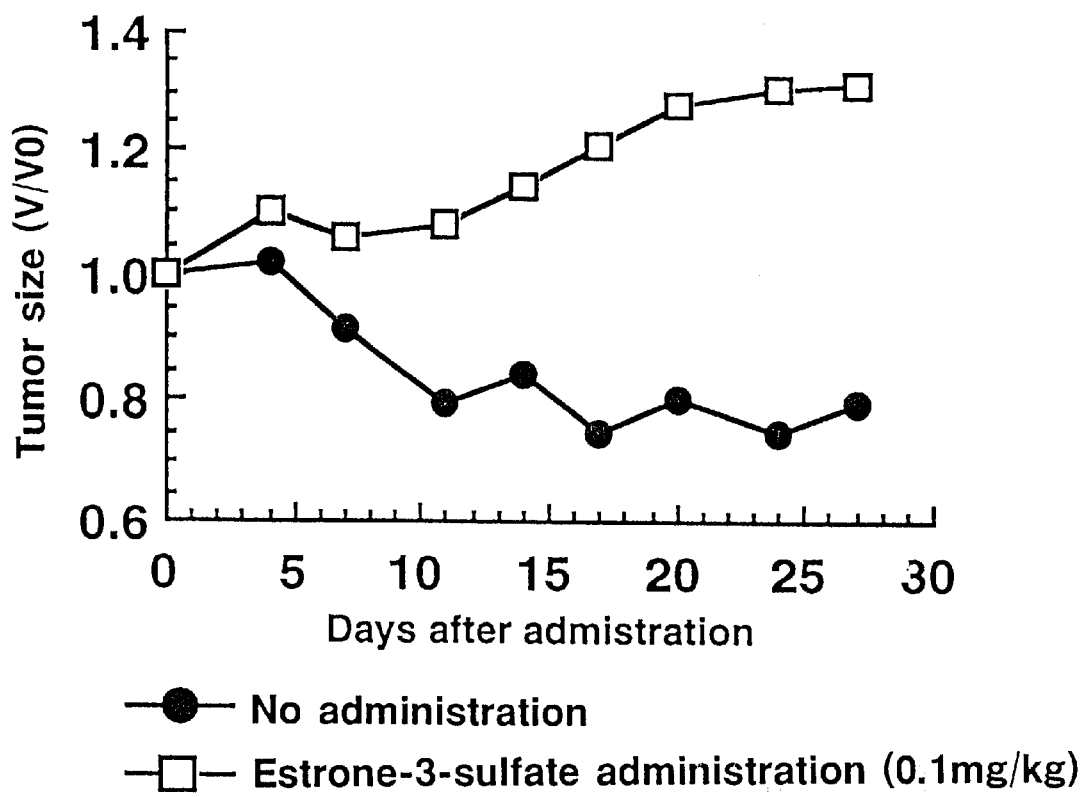
Fig. 3  Tumor growth by transformed cells transplanted into nude mice

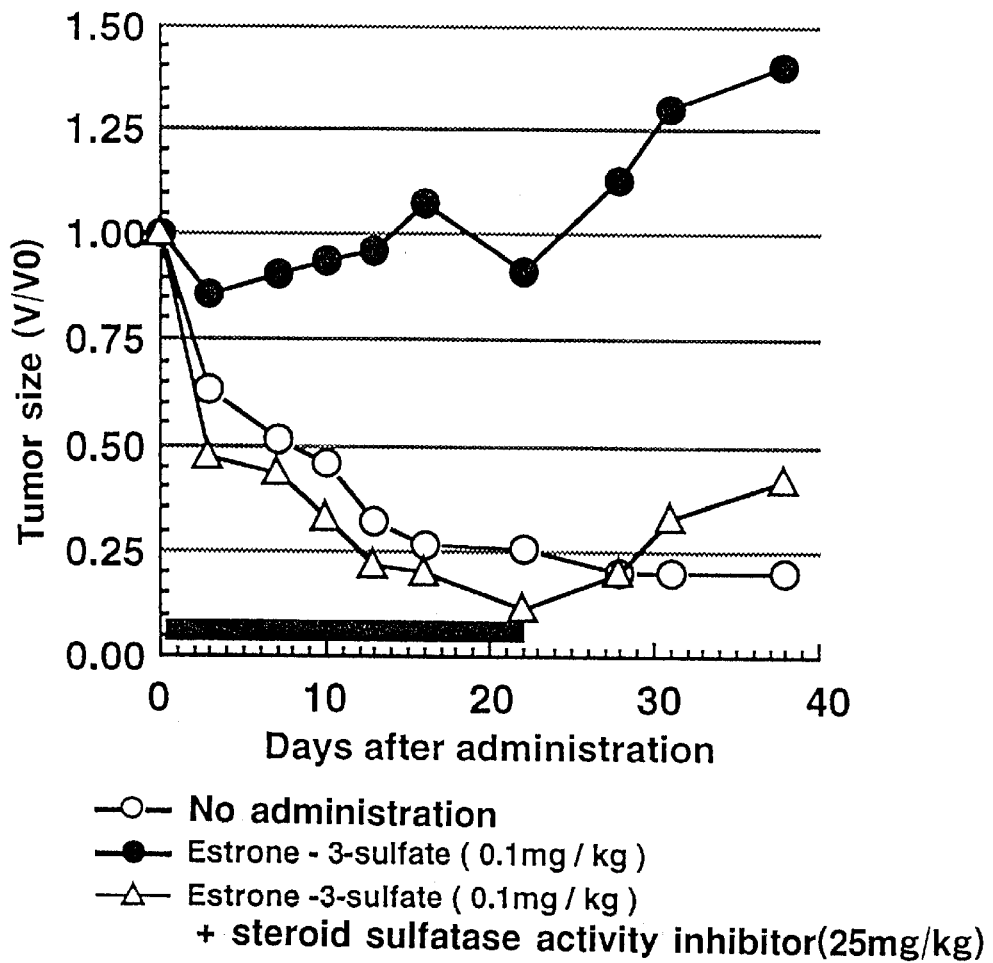
Fig. 4 Anti-tumor effect of steroid sulfatase activity inhibitor

METHOD FOR SEARCHING STEROID SULFATASE INHIBITORS

TECHNICAL FIELD

The present invention provides a method of screening for compounds which inhibit steroid sulfatase activity related to the biosynthesis of steroid hormones with the aim of healing hormone-dependent diseases such as breast cancer.

BACKGROUND ART

It has been known for long that anti-hormone agents are effective against hormone-dependent cancers, and anti-male sex hormone agents and anti-female sex hormone agents have been used for treating them. Recently, tamoxifen, which is an anti-hormone agent, has been developed as an anti-tumor agent for hormone-dependent cancers (Iacobelli, S., et al., The Role of Tamoxifen in Breast Cancer, Raven Press, NY, 1982). For the biosynthesis of steroid hormones, specifically, estrogen, two pathways are known; i.e., the aromatase pathway through which androstenedione is converted into estrone and the sulfatase pathway through which estrone-sulfate is converted into estrone. In recent years, rapid progress has been made in the research and development of aromatase inhibitors which suppress the estrone biosynthesis by blocking the aromatase pathway.

For example, there have been reported screening systems using, as markers, the inhibition of the growth of cells carrying an introduced aromatase gene [Cancer Res., 50, 6949 (1990); J. Steroid Biochem. Molec. Biol., 44, 611 (1993); PCT National Publication No. 502261/92] and the reduction in the volume of a tumor established by transplanting cells carrying an introduced aromatase gene into a nude mouse [Cancer Res., 55, 3073 (1995)].

However, with the development of analytical research on the steroid hormone biosynthetic systems, it has become clear that the steroid sulfatase pathway plays a more important role than the aromatase pathway in the estrone biosynthesis [J. Clin. Endocrinol. Metab., 59, 29 (1984); Ann. NY Acad. Sci., 464, 126 (1986); J. Steroid Biochem., 34, 155 (1989)].

Recently, reports have been made of attempts to screen steroid sulfatase inhibitors by assay systems using a fraction having steroid sulfatase activity obtained by fractionating human placenta rich in steroid sulfatase [Steroids, 58, 106 (1993); J. Steroid Biochem. Molec. Biol., 48, 523 (1994); J. Steroid Biochem. Molec. Biol., 59, 41 (1996); Biochemistry, 36, 2586 (1997)]. It is also reported that steroid sulfatase inhibitors can be screened and evaluated by not only the inhibiting activity on a fraction having the enzyme activity, but also the growth inhibition against cells, showing hormone-dependent growth [J. Steroid Biochem. Molec. Biol., 59, 83 (1996); Cancer Res., 57, 702 (1997)]. A steroid sulfatase gene derived from human is known [J. Biol. Chem., 264, 13865 (1989)].

However, the screening systems using a fraction having the enzyme activity and cells showing hormone-dependent growth are not sufficient in sensitivity. Further, there exists a need for a screening system using animals which can be models of actual conditions of diseases.

DISCLOSURE OF THE INVENTION

An object of the present invention is to provide a method of efficiently screening for compounds inhibiting steroid sulfatase activity which are useful for the treatment of hormone-dependent diseases such as breast cancer.

The present invention relates to a method of screening for steroid sulfatase inhibitors by using the inhibiting activity on the growth of cells carrying an introduced steroid sulfatase gene as a marker. More specifically, the present invention relates to a method of screening for steroid sulfatase inhibitors by causing a test compound to act on cells carrying an introduced steroid sulfatase gene and estimating the inhibiting activity of the compound on the growth of the cells. The present invention also relates to a method of screening for steroid sulfatase inhibitors by transplanting cells carrying an introduced steroid sulfatase gene into an animal, causing a test compound to act on the animal, and estimating the inhibiting activity of the compound on the growth of the cells. Further, the present invention relates to steroid sulfatase inhibitors obtained by the above screening methods. However, known steroid sulfatase inhibitors are excluded from the above-mentioned steroid sulfatase inhibitors which are one of the aspects of the present invention.

In the present invention, any gene can be used that encodes a polypeptide having steroid sulfatase activity. Examples of suitable genes include a gene encoding a polypeptide comprising the amino acid sequence shown in SEQ ID NO: 1, and a gene encoding a polypeptide which has an amino acid sequence wherein one or more amino acid residues are deleted, substituted or added in the amino acid sequence of a polypeptide having the amino acid sequence shown in SEQ ID NO: 1 and which has steroid sulfatase activity.

The polypeptides having an amino acid sequence wherein one or more amino acid residues are deleted, substituted or added in the amino acid sequence of the polypeptide and having steroid sulfatase activity can be prepared according to the methods described in Nucleic Acids Research, 10, 6487 (1982); Proc. Natl. Acad. Sci., USA, 79, 6409 (1982); Proc. Natl. Acad. Sci., USA, 81, 5662 (1984); Science, 224, 1431 (1984); WO85/00817; Nature, 316, 601 (1985); Gene, 34, 315 (1985); Nucleic Acids Research, 13, 4431 (1985); Current Protocols in Molecular Biology, the 8th chapter, Mutagenesis of Cloned DNA, John Wiley & Sons, Inc.; 1989, etc.

Specific examples of the genes encoding a polypeptide having steroid sulfatase activity useful in the present invention include DNA comprising the nucleotide sequence shown in SEQ ID NO: 2, and DNA which hybridizes to such DNA under stringent conditions and which encodes a polypeptide having steroid sulfatase activity.

The "DNA which is hybridizable under stringent conditions" refers to DNA which is obtained by colony hybridization, plaque hybridization or Southern blot hybridization using the DNA encoding a polypeptide having steroid sulfatase activity as a probe. Such DNA can be identified, for example, by performing hybridization at 65° C. in the presence of 0.7–1.0 M sodium chloride using a filter with colony- or plaque-derived DNA immobilized thereon and then washing the filter at 65° C. using 0.1 to 2-fold concentrated SSC solution (SSC solution: 150 mM sodium chloride and 15 mM sodium citrate) The hybridizable DNA is, for example, DNA having at least 60% homology, preferably 80% or more homology, more preferably 95% or more homology to the nucleotide sequence of DNA encoding a polypeptide having an amino acid sequence included in the amino acid sequence shown in SEQ ID NO: 1.

Hybridization can be carried out according to the methods described in Sambrook, Fritsch and Maniatis, edit., Molecular Cloning, A Laboratory Manual, Second Edition, Cold Spring Harbor Laboratory Press, 1989 (hereinafter abbreviated as Molecular Cloning, Second Edition), etc.

As the host cell for the introduction of the steroid sulfatase gene of the present invention, any bacterial cells, yeast cells, animal cells, insect cells, etc. can be used so far as they are capable of introduction of a steroid sulfatase gene and expression of steroid sulfatase. Preferred are cells showing hormone-dependent growth.

Of steroid sulfatases of the present invention, human-derived steroid sulfatase is reported to require post-translational modifications for the expression of the activity [Cell, 82, 271 (1998)], and in this case, an animal cell is used as the host cell. Examples of animal cells useful as the host cell include Namalwa cells, HBT5637 (Japanese Published Unexamined Patent Application No. 299/88), COS1 cells, COS7 cells and CHO cells. When cells carrying an introduced steroid sulfatase gene are transplanted into an animal such as a mouse and fixed therein to form a tumor, cells which show hormone-dependent growth and which are easily fixed in an animal to form a tumor are used. Suitable cells include MCF-7 [Int. J. Cancer, 54, 119 (1993)], T47D [J. Clin. Endocrinol., 55, 276 (1982)] and Ishikawa Strain [J. Steroid Biochem., 24, 85 (1986)].

When an animal cell is used as the host cell, the expression vectors that can be employed are those capable of autonomous replication or integration into chromosome in the host cell and comprising a promoter at a position appropriate for the transcription of a steroid sulfatase gene. Suitable vectors include pcDNAI, pcDNA3 and pcDM8 (all produced by Invitrogen), pAGE107 [Japanese Published Unexamined Patent Application No. 22979/91; Cytotechnology, 3, 133 (1990)], pAS3-3 (Japanese Published Unexamined Patent Application No. 227075/90), pCDM8 [Nature, 329, 840 (1987)], pcDNAI/Amp (Invitrogen), pREP (Invitrogen), pAGE103 [J. Biochem., 101, 1307 (1987)], etc.

As the promoter, any promoters capable of functioning in animal cells can be used. Suitable promoters include the promoter of IE (immediate early) gene of cytomegalovirus (human CMV), SV40 early promoter, metallothionein promoter, the promoter of a retrovirus, heat shock promoter, SR α promoter, etc. The enhancer of IE gene of human CMV may be used in combination with the promoter.

Introduction of the recombinant vector into animal cells can be carried out by any of the methods for introducing DNA into animal cells, for example, electroporation [Cytotechnology, 3, 133 (1990)], the calcium phosphate method (Japanese Published Unexamined Patent Application No. 227075/90) and lipofection method [Proc. Natl. Acad. Sci., USA, 84, 7413 (1987)]. Transformed cells can be obtained and cultured according to the method described in Japanese Published Unexamined Patent Application No. 227075/90 or Japanese Published Unexamined Patent Application No. 257891/90.

When an insect cell is used as the host cell, steroid sulfatase can be expressed in the insect cell by using the methods described in Baculovirus Expression Vectors, A Laboratory Manual, W. H. Freeman and Company, New York (1992); Current Protocols in Molecular Biology, Supplement 38, 28, Unit 16.9, 16.11, John Wiley and Sons, New York (1995); Bio/Technology, 6, 47 (1998), etc. That is, a vector carrying an introduced steroid sulfatase gene and a baculovirus are cotransfected into an insect cell, the insect cell is cultured to obtain a recombinant virus from the culture supernatant, and then an insect cell is infected with the recombinant virus, whereby steroid sulfatase can be expressed in the insect cell.

Examples of the vectors suitable for use in this method are pVL1392, pVL1393 and pBlueBacIII (all produced by Invitrogen). An example of the baculovirus is *Autographa californica* nuclear polyhedrosis virus, which is a virus infecting insects belonging to the family Barathra.

Examples of the insect cells useful as the host cell are Sf9 and Sf21 which are ovarian cells of *Spodoptera frugiperda* (Baculovirus Expression Vectors, A Laboratory Manual, W. H. Freeman and Company, New York, 1992) and High 5 which is ovarian cells of *Trichoplusia ni* (Invitrogen).

Cotransfection of the vector carrying the introduced recombinant gene and the baculovirus into an insect cell for the preparation of the recombinant virus can be carried out by the calcium phosphate method (Japanese Published Unexamined Patent Application No. 227075/90), lipofection method [Proc. Natl. Acad. Sci., USA, 84, 7413 (1987)], etc.

When a yeast cell is used as the host cell, YEp13 (ATCC 37115), YEp24 (ATCC 37051), YCp (ATCC 37419), etc. can be used as the expression vector.

As the promoter, any promoters capable of functioning in yeast cells can be used. Suitable promoters include PHO5 promoter, PGK promoter, GAP promoter, ADH promoter, gal1 promoter, gal10 promoter, heat shock protein promoter, MF α1 promoter, CUP1 promoter, etc.

Examples of the yeast cells useful as the host cell include cells of *Saccharomyces cerevisiae, Schizosaccharomyces pombe, Kluyveromyces lactis, Trichosporon pullulans* and *Schwanniomyces alluvius*.

Introduction of the recombinant vector can be carried out by any of the methods for introducing DNA into yeast cells, for example, electroporation [Methods. Enzymol., 194, 182 (1990)], the spheroplast method [Proc. Natl. Acad. Sci., USA, 84, 1929 (1978)] and the lithium acetate method [J. Bacteriol., 153, 163 (1983); Proc. Natl. Acad. Sci., USA, 75, 1929 (1978)].

When the gene is expressed in a yeast cell, an animal cell or an insect cell, a glycosylated polypeptide can be obtained.

When a procaryotic cell such as a bacterial cell is used as the host cell, it is preferred that the expression vector for the steroid sulfatase gene should be capable of autonomous replication in the host cell and that the expression vector should comprise a promoter, a ribosome binding sequence, DNA encoding steroid sulfatase and a transcription termination sequence. The vector may further comprise a gene regulating the promoter.

Examples of suitable expression vectors are pBTrp2, pBTac1 and pBTac2 (all produced by Boehringer Mannheim), pSE280 (Invitrogen), pGEMEX-1 (Promega), pQE-8 (QIAGEN), pKYP10 (Japanese Published Unexamined Patent Application No. 110600/83), pKYP200 [Agric. Biol. Chem., 48, 669 (1984)], pLSA1 [Agric. Biol. Chem., 53, 277 (1989)], pGEL1 [Proc. Natl. Acad. Sci., USA, 82, 4306 (1985)], pBluescript (Stratagene), pTrs30 (FERM BP-5407), pTrs32 (FERM BP-5408), pGHA2 (FERM BP-400), pGKA2 (FERM BP-6798), pTerm2 (Japanese Published Unexamined Patent Application No. 22979/91, U.S. Pat. No. 4,686,191, U.S. Pat. No. 4,939,094, U.S. Pat. No. 5,160,735), pKK233-2 (Pharmacia), pGEX (Pharmacia), pET system (Novagen), pUB110 [described in Recombinant DNA Techniques (1983), Addison-Wesley Pub. Co.] and pSupex [J. Bacteriol., 172, 2392 (1990)].

As the promoter, any promoters capable of functioning in host cells such as *Escherichia coli* can be used. For example, promoters derived from *Escherichia coli* or phage, such as trp promoter (Ptrp), lac promoter (Plac), $P_L$ promoter, $P_R$ promoter, PletI promoter and $P_{SE}$ promoter, SPO1 promoter, SPO2 promoter and penP promoter can be used. Artificially designed or modified promoters such as a promoter in which two Ptrp are combined in tandem (Ptrp×2) and tac promoter, etc. can also be used.

It is preferred to use a plasmid in which the distance between the Shine-Dalgarno sequence (ribosome binding sequence) and the initiation codon is adjusted to an appropriate length (e.g., 6–18 bases).

The transcription termination sequence is not essential for the expression of the steroid sulfatase gene of the present invention, but it is preferred that the transcription termination sequence lie immediately downstream of the structural gene.

Examples of the procaryotes useful as the host cell are microorganisms belonging to the genera Escherichia, Serratia, Corynebacterium, Brevibacterium, Pseudomonas, Bacillus and Microbacterium, specifically, *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Serratia marcescens* OUT8259, *Pseudomonas putida* ATCC 12633, *Bacillus subtilis* ATCC 33677, *Bacillus amyloliquefaciens, Brevibacterium ammoniagenes, Brevibacterium immariophilum* ATCC 14068, *Brevibacterium saccharolyticum* ATCC 14066, *Brevibacterium flavum* ATCC 14067, *Brevibacterium lactofermentum* ATCC 13869, *Corynebacterium glutamicum* ATCC 13032, *Corynebacterium acetoacidophilum* ATCC 13870 and *Microbacterium ammoniaphilum* ATCC 15354. Preferred are *Escherichia coli* XL1-Blue, *Escherichia coli* XL2-Blue, *Escherichia coli* DH1 and *Escherichia coli* MC1000.

Introduction of the recombinant vector can be carried out by any of the methods for introducing DNA into the above host cells, for example, the method using calcium ion [Proc. Natl. Acad. Sci., USA, 69, 2110 (1972)] and the protoplast method [Japanese Published Unexamined Patent Application No. 248394/88; Gene, 17, 107 (1982); Molecular & General Genetics, 168, 111 (1979)].

Introduction of the steroid sulfatase gene into the above host cells can be carried out by the methods described in Molecular Cloning, Second Edition; Current Protocols in Molecular Biology, Supplement 1–34, John Wiley and Sons, New York (1995), etc. That is, DNA encoding steroid sulfatase is digested with a restriction enzyme or deoxyribonuclease, and the obtained DNA fragment containing the DNA encoding steroid sulfatase is inserted downstream of a promoter in an expression vector. Then, the expression vector containing the DNA is introduced into host cells, followed by selection of transformed cells carrying the introduced expression vector containing the steroid sulfatase gene.

Selection of cells carrying the introduced steroid sulfatase gene is carried out using the expression of the activity of a marker gene on the expression vector and the improvement of steroid sulfatase activity as markers. Measurement of the steroid sulfatase activity is carried out according to the method of Reed, et al. [Int. J. Cancer, 50, 901 (1992)].

For the culturing of the transformed cells prepared by using animal cells as the host cells, any media that can be assimilated by the animal cells can be used. Examples of suitable media include those generally used for culturing animal cells such as RPMI1640 medium [The Journal of the American Medical Association, 199, 519 (1967)], Eagle's MEM [Science, 122, 501 (1952)], DMEM [Virology, 8, 396 (1959)] and 199 medium [Proceeding of the Society for the Biological Medicine, 73, 1 (1950)], and media prepared by adding fetal calf serum or the like to these media.

Culturing is usually carried out at pH 6–8 at 30–40° C. for 1–7 days in the presence of 5% $CO_2$. If necessary, antibiotics such as kanamycin and penicillin may be added to the medium during the culturing.

Fetal calf sera which may be added to the medium are those containing no steroid in view of the examination of the hormone-dependent growth of cells. For example, a fetal calf serum freed of steroid compounds by treatment with activated carbon can be used. Commercially available ones such as Steroid-free calf serum (Hyclone, Calif.) can also be used.

As the selective marker for transformed cells, those existing on the respective expression vectors are used. Suitable markers include genes responsible for the resistance to hygromycin, G418, methotrexate, etc. Transformed cells can be selected based upon the appearance of resistance to these drugs caused by the expression of these selective markers. Genes coding for enzymes such as glutamine synthetase can also be used as selective markers.

Then, transformed cells are selected based upon the increase in steroid sulfatase activity. Measurement of the steroid sulfatase activity can be carried out according to the method of Vaccaro, et al. [Enzyme, 37, 115 (1987)] or that of Reed, et al. [Int. J. Cancer, 50, 901 (1992)] based upon the detection of estrone in a toluene-extracted fraction resulting from the conversion of tritium-labeled estrone-3-sulfate. The enzyme activity can also be measured using synthetic substrates such as 4-methyl-umbelliferyl sulfate [Experimentia, 35, 309 (1979)] and p-nitrophenyl sulfate [Padiat. Res., 11, 894 (1977)] in place of estrone-3-sulfate.

Examination of the hormone-dependent cell growth can be carried out by first culturing cells in an estrogen-free medium, then subculturing the cells in media containing estrogen compounds such as estrone-3-sulfate, estradiol and estrone at various concentrations, and observing the cell growth in the presence of each estrogen compound at each concentration to examine the dependence of the cell growth on the concentration of an estrogen compound.

It is preferred to use reagents of high purity as estrogen compounds. Specifically, in the case of estrone-3-sulfate, it is preferably used after being dissolved in distilled water, extracted at least twice with ether, and then freed of ether-soluble impurities.

Culturing of the transformed cells of the present invention can be carried out according to a usual method for culturing the host cells.

For the culturing of the transformed cells prepared by using insect cells as the host cells, any media that can be assimilated by the insect cells can be used. Examples of suitable media include those generally used for culturing insect cells such as TNM-FH medium (Pharmingen), Sf-900 II SFM medium (GIBCO) ExCell400 and ExCell405 (both produced by JRH Biosciences) and Grace's Insect Medium [Grace, T.C.C., Nature, 195, 788 (1962)]. Culturing is usually carried out at pH 6–7 at 25–30° C. for 1–5 days. If necessary, antibiotics such as gentamicin may be added to the medium during the culturing.

For the culturing of the transformed cells prepared by using procaryotic cells such as *Escherichia coli* cells or eucaryotic cells such as yeast cells as the host cells, any of natural media and synthetic media can be used insofar as it is a medium suitable for efficient culturing of the transformed cells which contains carbon sources, nitrogen sources, inorganic salts, etc. that can be assimilated by the host used.

Examples of suitable carbon sources include carbohydrates such as glucose, fructose, sucrose, molasses containing them, starch and starch hydrolyzate; organic acids such as acetic acid and propionic acid; and alcohols such as ethanol and propanol.

As the nitrogen sources, ammonia, ammonium salts of inorganic or organic acids such as ammonium chloride, ammonium sulfate, ammonium acetate and ammonium phosphate, and other nitrogen-containing compounds can be used as well as peptone, meat extract, yeast extract, corn steep liquor, casein hydrolyzate, soybean cake, soybean cake hydrolyzate and various fermented cells and digested products thereof.

Examples of the inorganic salts include potassium dihydrogenphosphate, dipotassium hydrogenphosphate, magnesium phosphate, magnesium sulfate, sodium chloride, ferrous sulfate, manganese sulfate, copper sulfate and calcium carbonate.

Culturing is usually carried out under aerobic conditions, for example, by shaking culture or submerged spinner culture under aeration, at 15–40° C. for 16–96 hours. The pH is maintained at 3.0–9.0 during the culturing. The pH adjustment is carried out by using an organic or inorganic acid, an alkali solution, urea, calcium carbonate, ammonia, etc. If necessary, antibiotics such as ampicillin and tetracycline may be added to the medium during the culturing.

When a microorganism transformed with an expression vector comprising an inducible promoter is cultured, an inducer may be added to the medium, if necessary. For example, in the case of a microorganism transformed with an expression vector comprising lac promoter, isopropyl-β-D-thiogalactopyranoside or the like may be added to the medium; and in the case of a microorganism transformed with an expression vector comprising trp promoter, indoleacrylic acid or the like may be added.

Screening for steroid sulfatase inhibitors can be carried out by causing a test compound to act on the transformed cells obtained above and estimating the inhibiting activity of the compound on the growth of the cells. The transformed cells to be acted on by a test compound may be either those cultured in vitro or those transplanted into an animal.

Screening by the use of the cells cultured in vitro can be carried out in the following manner.

First, the number of living transformed cells in a test tube is estimated and then a test compound is added to the cells. After culturing for a certain period, the number of living cells is estimated. The steroid sulfatase-inhibiting activity of the test compound can be estimated by comparing the cell growth in the presence of the test compound with that in the absence of the test compound.

Screening by the use of the animal cells transplanted into an animal can be carried out in the following manner.

First, cells carrying the introduced steroid sulfatase gene are transplanted into an animal such as a mouse for fixation to form a tumor. That is, tumor cells carrying the introduced steroid sulfatase gene are transplanted subcutaneously into an immunodeficient mouse, for example, a BALB/c-nu/nu (a nude mouse) or an SCID mouse in an amount of $1-5 \times 10^6$ cells to form a tumor. At the time of transplantation, a crude extract of basement membrane containing adhesion factor (e.g., matrigel-basement membrane, Becton & Dickinson) may be added in order to improve the fixation rate [Br. J. Cancer, 67, 953 (1993)]. In the case of estrogen-dependent breast cancer, the fixation rate is improved and the tumor growth after the fixation is promoted by administering an estrogen compound.

Screening for steroid sulfatase inhibitors by the use of the animal cells can be carried out in the following manner.

The volume of a tumor can be calculated from the shorter diameter and the longer diameter of the tumor measured with slide calipers according to the following approximation formula.

$$\text{Tumor volume} = (\text{longer diameter}) \times (\text{shorter diameter})^2 \div 2$$

Animals in which the tumor growth was confirmed after administration of estrone-3-sulfate are selected, and a test compound is administered thereto. Then, the tumor volume is measured to estimate the steroid sulfatase-inhibiting activity of the test compound. The test compound may be administered by any of intravenous, subcutaneous, intraperitoneal and oral routes. The steroid sulfatase-inhibiting activity of the compound can be estimated by measuring the tumor volume at intervals of 3–4 days after the administration, and then comparing the tumor growth between the group to which only estrone-3-sulfate was administered and the group to which estrone-3-sulfate and the test compound were administered.

Certain embodiments of the present invention are illustrated in the following examples. When a kit was used in the following examples, the experiment was carried out according to the attached protocol unless otherwise specified.

BRIEF DESCRIPTION OF THE DRAWINGS

FIG. 1 shows the steroid sulfatase activity of parent cell lines and cell lines transformed by steroid sulfatase gene.

FIG. 2 shows the change in the dependence of growth of transformed cell line T8S-2 and parent cell line T47D on estrogen compounds. The symbols respectively designate the cell growth in the presence of the following estrogen compounds: open square, estrone; filled circle, estradiol; and filled square, estrone-3-sulfate.

FIG. 3 shows the change in the tumor volume after the transplantation of transformed cell line into mice. The symbols respectively designate the data on the following test groups: open square, estrone-3-sulfate-administered group; and filled circle, group with no administration.

FIG. 4 shows the anti-tumor effect of a steroid sulfatase inhibitor. The symbols respectively designate the data on the following test groups: open circle, group with no administration; filled circle, estrone-3-sulfate-administered group; and open triangle, group to which estrone-3-sulfate and steroid sulfatase inhibitor C14 were simultaneously administered.

BEST MODES FOR CARRYING OUT THE INVENTION

EXAMPLE 1

Construction of Cells Carrying an Introduced Human Steroid Sulfatase Gene

Plasmid pSVL-STS containing a human-derived steroid sulfatase gene (hereinafter abbreviated as STS) [J. Biol. Chem., 26, 13865 (1989)] was digested with restriction enzymes XbaI and BamHI, and the digested DNA fragments were separated by agarose gel electrophoresis. The gel portion which contains a fragment of ca. 2.4 kb containing STS was cut out, followed by extraction of the fragment. The obtained DNA fragment was inserted between the XbaI site and the BamHI site of pAGE248 [J. Biochem., 110, 1307 (1987)], which is an expression vector for animal cells, and *Escherichia coli* (DH5 α strain, GIBCO) was transformed using the vector carrying the introduced DNA fragment. A plasmid was extracted from the transformant using a plasmid extraction kit (Qiagen) to obtain pAGE248-STS. In the same manner, the above DNA fragment was inserted between the XbaI site and the BamHI site of subcloning plasmid pBlueScriptIISK(-) (Stratagene) to obtain recombinant plasmid pBS-STS. The plasmid pBS-STS was cleaved with NotI and XhoI to obtain a fragment containing STS in the same manner as above. The fragment containing STS was inserted between the NotI site and the XhoI site of pcDNA3 (Invitrogen), which is an expression vector for animal cells, to prepare expression plasmid pcSTS.

The above procedure for preparing recombinant plasmids was carried out using 100 ng of vector DNA cleaved with restriction enzymes and extracted and 100 ng of a DNA fragment containing STS. These DNAs were ligated using DNA ligation kit ver. 1 (Takara Shuzo Co., Ltd.).

These expression plasmids containing STS were introduced into T47D cell and MCF7 cell by electroporation using GenePulser (BioRad) and a cuvette 0.2 cm in width (BioRad) in the following manner.

The cells for gene introduction were previously subcultured in RPMI1640 medium (GIBCO) supplemented with 10% fetal calf serum (Hyclone), $10^{-10}$ M estradiol (Sigma), 50 U/ml penicillin G (GIBCO) and 50 μg/ml streptomycin sulfate (GIBCO) To 200 μgl/cuvette of a cell suspension (containing $1.6 \times 10^6$ cells in a buffer comprising 137 mM potassium chloride, 2.7 mM sodium chloride, 8.1 mM disodium hydrogenphosphate, 1.5 mM potassium dihydrogenphosphate and 4 mM magnesium chloride) was added 4 μg of the expression plasmid, followed by application of electric pulses at 0.30 kV, 125 μFD and intervals of 2.3–2.5 msec. After the pulses were applied, the cuvette was allowed to stand on ice for 5 minutes. The cell suspension in the cuvette was diluted with 10 ml of RPMI1640 medium containing 10% fetal calf serum. The diluted suspension was pipetted into wells of a 96-well plate (Nunc) in an amount of 100 μl per well, followed by culturing in a 5% $CO_2$-incubator at 37° C. After culturing for one day, hygromycin B (Wako Pure Chemical Industries, Ltd.) was added to the cells carrying the introduced pAGE-derived vector to a concentration of 300 μg/ml and G418 (Sigma) was added to the cells carrying the introduced pcDNA3-derived vector to a concentration of 0.6 mg/ml, followed by further culturing. After culturing for three weeks, the medium was replaced by a medium prepared by adding $10^{-10}$ M estrone-3-sulfate (Sigma) extracted with ether and 300 μg/ml hygromycin B or 0.6 mg/ml G418 to PRF-MEM [a medium prepared by adding 110 μg/ml sodium pyruvate, 1×Non Essential amino acids (ICN) and 5% steroid-free fetal calf serum to Eagle's MEM (Nissui Pharmaceutical Co., Ltd.)], followed by further culturing. Subculturing was repeated with dilution of the culture, and 7 weeks after the gene introduction, transformed cell lines which were resistant to hygromycin B or G418 and which grew in the presence of a low concentration of estrone-3-sulfate were selected.

The steroid-free fetal calf serum employed above was prepared in the following manner.

Activated carbon (0.5 g, Wako Pure Chemical Industries, Ltd.), 5 mg of dextran T-70 (Pharmacia) and 50 ml of 50 mM Tris-hydrochloride buffer (pH. 8.0) were mixed thoroughly. The resulting mixture was centrifuged at room temperature and the precipitate was recovered to obtain a dextran-coated activated carbon. To this carbon was added 100 ml of a fetal calf serum, and the resulting mixture was allowed to stand at 45° C. for 30 minutes and then centrifuged. The obtained supernatant was filtered with a 0.1 μm filter and sterilized to prepare a steroid-free fetal calf serum.

Estrone-3-sulfate (Sigma, containing 30% Tris as a stabilizer) was treated with ether, prior to use, to remove estrone compounds contained in trace amounts. Specifically, a 10 mM aqueous solution of estrone-3-sulfate was extracted twice with 5-fold amount of diethyl ether, and the water layer was freeze-dried and stored at -20° C.

EXAMPLE 2

Selection of Transformed Cells

Cells carrying the introduced STS were selected in the following manner by measuring the steroid sulfatase activity of the transformed cells obtained in Example 1.

The transformed cells selected in Example 1 were cultured in RPMI1640 medium using F25 flask (Greiner). When the cells grew to the extent that they covered 60–80% of the inner surface of the flask, the medium was removed and the cells were washed with physiological saline, followed by replacement of the medium by 5 ml of a serum-free PRF-MEM. To the flask was added 5 pmol of [6,7-$^3$H] estrone-3-sulfate (NEN) to a final concentration of $10^{-9}$ M, followed by culturing in a 5% $CO_2$-incubator for 4 hours. After the culturing, a 1 ml aliquot of the culture supernatant was taken, and 5 ml of toluene and then $4.5 \times 10^3$ dpm [4-$^{14}$C]estrone as an internal standard were added thereto, followed by thorough stirring for 30 seconds. The resulting mixture was allowed to stand for 20 minutes and separated into the water layer and the organic solvent layer. The solvent fraction (2 ml) was concentrated to a volume of 100 μl by centrifugal concentration. The radioactivity of $^3$H and $^{14}$C in the concentrate was measured using toluene containing 4 g/l OMNIFLUOR (NEN) as a scintillator. The enzyme activity of the cells was measured from the conversion of [6,7-$^3$H]estrone-3-sulfate which is a water-soluble substrate into [6,7-$^3$H]estrone which is a toluene-soluble reaction product. The extraction efficiency was corrected using the added internal standard and the amount of the converted substrate was calculated. The results are shown in FIG. 1. In FIG. 1, T8S-2 cell line is the transformed cell line prepared by introducing plasmid pAGE248-STS into T47D cell line, MCS-1 cell line and MCS-5 cell line are the transformed cell lines respectively prepared by introducing plasmid pcSTS into MCF-7 cell line, and M8S-1 cell line is the transformed cell line prepared by introducing pAGE248-STS into MCF-7 cell line. As is clear from FIG. 1, the introduction of STS resulted in 30 to 40-fold enhancement of the enzyme activity.

EXAMPLE 3

Verification of Hormone-Dependent Growth

Parent cell line T47D and transformed cell line T8S-2 carrying the introduced STS were respectively subcultured in RPMI1640 medium. When the cultured cells grew to the extent that they covered 80% of the inner surface of a 5-cm Petri dish, the medium was replaced by estrogen-free PRF-MEM. After culturing in a 5% $CO_2$-incubator for 5 days, the cells were released with an EDTA-trypsin solution (GIBCO). The cells were put into wells of a 96-well plate in an amount of 5×10³ cells per well, and 100 μl portions of PRF-MEM containing estrone, estradiol or estrone-3-sulfate at varied concentrations were added thereto, followed by incubation in a 5% $CO_2$-incubator (final concentration of each estrogen compound: $10^{-13}$–$10^{-7}$ M). After 7 days, 10 μl of Alamar Blue reagent (BIO SOURCE) was added to each well with gentle mixing. After culturing for 3 hours, the absorbance at 560 nm was measured as the relative value for the number of the cells with the absorbance at 620 nm as a control.

FIG. 2 shows the growth of the parent cell line and the transformed cell line in media containing estrogen compounds at various concentrations. In FIG. 2, T47D cell line is the parent cell line and T8S-2 cell line is the transformed cell line prepared by introducing plasmid pAGE248-STS into T47D cell line.

As shown in FIG. 2, the cell line carrying the introduced STS was capable of growing in the presence of estrone-3-sulfate at concentrations as low as 1/10–1/100 as compared with the case of the parent cell line. The cell line prepared by introducing only a vector into the parent cell line exhibited the same estrogen compound-dependent growth as the parent cell line. It indicates that the screening system for steroid sulfatase inhibitors based upon the growth of cells carrying an introduced STS can detect the inhibiting activity of test compounds at low concentrations.

EXAMPLE 4

Formation of a Tumor after Transplantation of Cells Carrying an Introduced Steroid Sulfatase Gene The transformed cell line proved to show hormone-dependent growth in Example 3 was subcultured in RPMI1640 medium, and the cells were released with an EDTA-trypsin solution (GIBCO) and washed with RPMI1640 medium. The cells were suspended at a concentration of 2×10⁸ cells/ml and the suspension was mixed with an equal volume of matrigel-basement membrane (Becton & Dickinson). The resulting mixture was subcutaneously transplanted into 7- to 8-weeks-old female BALB/c-nu/nu mice, (nude mice, each group consisting of 5 mice) in an amount of 0.1 ml (1×10⁷ cells). On the day of transplantation and 2 weeks later, an estrogen preparation (EP depo, Teikoku Zoki) was intramuscularly administered. Mice in which the fixation of a tumor was confirmed were selected, and estrone-3-sulfate was subcutaneously administered to them every day in an amount of 0.1 mg/kg, beginning at the time when the tumor growth stopped after the final administration of estrogen preparation. FIG. 3 shows the tumor formation by the transformed cell line after the administration of estrone-3-sulfate. In the groups to which estrone-3-sulfate was not administered, the tumor did not grow at all but gradually reduced, and in some mice, the tumor disappeared. On the other hand, in the estrone-3-sulfate-administered groups, the tumor grew in all mice and there was no reduction of tumor. This result indicates that the transformed cell line transplanted into nude mice grows in the estrone-3-sulfate-dependent manner.

EXAMPLE 5

Effect of a Steroid Sulfatase Activity Inhibitor

The mice showing estrone-3-sulfate-dependent tumor growth obtained in Example 4 were divided into (1) a group with no administration, (2) an estrone-3-sulfate-administered group and (3) a group to which estrone-3-sulfate and a steroid sulfatase inhibitor were administered, each group consisting of 9 mice. To group (2) was administered 0.1 mg/kg estrone-3-sulfate and to group (3) were administered 0.1 mg/kg estrone-3-sulfate and 25 mg/kg compound C14 which is a steroid sulfatase inhibitor [Cancer Res., 57, 702 (1997)]. Administration was made subcutaneously for 22 days. Measurement of the tumor size was carried out until the 38th day after the start of administration. The results are shown in FIG. 4. The tumor volume in the estrone-3-sulfate-administered group became 1.4 times the initial volume by the 38th day, while that in the group with no administration became one-fifth the initial volume due to exhaustion of the hormone. Administration of both steroid sulfatase inhibitor and estrone-3-sulfate resulted in the reduction of tumor similar to that in the group with no administration.

Industrial Applicability

The present invention provides a method of efficiently screening for compounds inhibiting steroid sulfatase activity which are useful for the treatment of hormone-dependent diseases such as breast cancer and the like.

---

What is claimed is:

1. A method of screening for candidate steroid sulfatase inhibitors which comprises the steps of:
   transforming cells which show hormone-dependent growth with a steroid sulfatase coding sequence or DNA selected from the group consisting of a coding sequence encoding a polypeptide which comprises the amino acid sequence of SEQ ID NO:1, a coding sequence encoding a polypeptide which is at least 95% homologous to the amino acid sequence of SEQ ID NO:1 and which has steroid sulfatase activity, DNA comprising the nucleotide sequence of SEQ ID NO:2, and DNA which hybridizes to the DNA comprising the nucleotide sequence of SEQ ID NO:2 under stringent conditions and which encodes a polypeptide having steroid sulfatase activity;
   culturing transformed cells in vitro in the presence of an estrogen compound and a test compound;
   culturing transformed cells in vitro in the presence of an estrogen compound but in the absence of said test compound; and
   measuring the growth of the transformed cells cultured in the presence of the test compound and the growth of the transformed cells cultured in the absence of the test compound,
   whereby a test compound that inhibits the growth of the transformed cells compared to the growth in the absence of the test compound is identified as a candidate steroid sulfatase inhibitor.

2. A method of screening for candidate steroid sulfatase inhibitors which comprises the steps of:
   transforming cells which show hormone-dependent growth with a steroid sulfatase coding sequence or DNA selected from the group consisting of a coding sequence encoding a polypeptide which comprises the amino acid sequence of SEQ ID NO:1, a coding sequence encoding a polypeptide which is at least 95% homologous to the amino acid sequence of SEQ ID NO:1 and which has steroid sulfatase activity, DNA comprising the nucleotide sequence of SEQ ID NO:2, and DNA which hybridizes to the DNA comprising the nucleotide sequence of SEQ ID NO:2 under stringent conditions and which encodes a polypeptide having steroid sulfatase activity;
   culturing transformed cells in vitro in the presence of estrone-3-sulfate and a test compound;
   culturing transformed cells in vitro in the presence of estrone-3-sulfate but in the absence of said test compound; and
   measuring the growth of the transformed cells cultured in the presence of the test compound and the growth of the transformed cells cultured in the absence of the test compound, whereby a test compound that inhibits the growth of the transformed cells compared to the growth in the absence of the test compound is identified as a candidate steroid sulfatase inhibitor.

3. A method of screening for candidate steroid sulfatase inhibitors which comprises the steps of:

transforming cells which show hormone-dependent growth and which can be fixed in an animal to form a tumor with a steroid sulfatase coding sequence or DNA selected from the group consisting of a coding sequence encoding a polypeptide which comprises the amino acid sequence of SEQ ID NO:1, a coding sequence encoding a polypeptide which is at least 95% homologous to the amino acid sequence of SEQ ID NO:1 and which has steroid sulfatase activity, DNA comprising the nucleotide sequence of SEQ ID NO:2, and DNA which hybridizes to the DNA comprising the nucleotide sequence of SEQ ID NO:2 under stringent conditions and which encodes a polypeptide having steroid sulfatase activity;

transplanting the transformed cells into two groups of immunodeficient mice to form a tumor;

administering estrone-3-sulfate to one group of mice;

administering a test compound and estrone-3-sulfate to the other group of mice;

measuring tumor growth in the first group of mice and tumor growth in the second group of mice, whereby a test compound that inhibits the tumor growth in the first group of mice compared to the tumor growth in the second group of mice is identified as a candidate steroid sulfatase inhibitor.

4. A cell showing steroid hormone-dependent growth and comprising an introduced steroid sulfatase coding sequence or DNA selected from the group consisting of a coding sequence encoding a polypeptide which comprises the amino acid sequence of SEQ ID NO: 1, a coding sequence encoding a polypeptide which is a least 95% homologous to the amino acid sequence of SEQ ID NO: 1 and which has steroid sulfatase activity, DNA comprising the nucleotide sequence of SEQ ID NO:2, and DNA which hybridizes to the DNA comprising the nucleotide sequence of SEQ ID NO:2 under stringent conditions and which encodes a polypeptide having steroid sulfatase activity.

5. The cell according to claim 4 wherein the cell is an animal cell.

6. The cell according to claim 4 or 5 wherein the cell is selected from the group consisting of T8S-2, MCS-1 and M8S-1.

* * * * *

UNITED STATES PATENT AND TRADEMARK OFFICE
CERTIFICATE OF CORRECTION

PATENT NO. : 6,585,954 B1 Page 1 of 1
DATED : July 1, 2003
INVENTOR(S) : Hideharu Anazawa et al.

It is certified that error appears in the above-identified patent and that said Letters Patent is hereby corrected as shown below:

<u>Title page,</u>
Item [56], References Cited, OTHER PUBLICATIONS, second reference, "effecr" should read -- effect --.

<u>Column 8,</u>
Line 64, "Chem., 26," should read -- Chem., 264, --.

<u>Column 9,</u>
Line 31, "(GIBCO)" should read -- (GIBCO). --.

<u>Column 22,</u>
Line 12, "a least" should read -- at least --.

Signed and Sealed this

Twenty-seventh Day of January, 2004

JON W. DUDAS
*Acting Director of the United States Patent and Trademark Office*

SEQUENCE LISTING

<160> NUMBER OF SEQ ID NOS: 2

<210> SEQ ID NO 1
<211> LENGTH: 583
<212> TYPE: PRT
<213> ORGANISM: Homo sapiens

<400> SEQUENCE: 1

Met Pro Leu Arg Lys Met Lys Ile Pro Phe Leu Leu Leu Phe Phe Leu
 1               5                   10                  15

Trp Glu Ala Glu Ser His Ala Ala Ser Arg Pro Asn Ile Ile Leu Val
                20                  25                  30

Met Ala Asp Asp Leu Gly Ile Gly Asp Pro Gly Cys Tyr Gly Asn Lys
            35                  40                  45

-continued

```
Thr Ile Arg Thr Pro Asn Ile Asp Arg Leu Ala Ser Gly Gly Val Lys
 50                  55                  60

Leu Thr Gln His Leu Ala Ala Ser Pro Leu Cys Thr Pro Ser Arg Ala
 65                  70                  75                  80

Ala Phe Met Thr Gly Arg Tyr Pro Val Arg Ser Gly Met Ala Ser Trp
                 85                  90                  95

Ser Arg Thr Gly Val Phe Leu Phe Thr Ala Ser Ser Gly Gly Leu Pro
            100                 105                 110

Thr Asp Glu Ile Thr Phe Ala Lys Leu Leu Lys Asp Gln Gly Tyr Ser
            115                 120                 125

Thr Ala Leu Ile Gly Lys Trp His Leu Gly Met Ser Cys His Ser Lys
130                 135                 140

Thr Asp Phe Cys His His Pro Leu His His Gly Phe Asn Tyr Phe Tyr
145                 150                 155                 160

Gly Ile Ser Leu Thr Asn Leu Arg Asp Cys Lys Pro Gly Glu Gly Ser
                165                 170                 175

Val Phe Thr Thr Gly Phe Lys Arg Leu Val Phe Leu Pro Leu Gln Ile
            180                 185                 190

Val Gly Val Thr Leu Leu Thr Leu Ala Ala Leu Asn Cys Leu Gly Leu
            195                 200                 205

Leu His Val Pro Leu Gly Val Phe Phe Ser Leu Phe Leu Ala Ala
    210                 215                 220

Leu Ile Leu Thr Leu Phe Leu Gly Phe Leu His Tyr Phe Arg Pro Leu
225                 230                 235                 240

Asn Cys Phe Met Met Arg Asn Tyr Glu Ile Ile Gln Gln Pro Met Ser
                245                 250                 255

Tyr Asp Asn Leu Thr Gln Arg Leu Thr Val Glu Ala Ala Gln Phe Ile
            260                 265                 270

Gln Arg Asn Thr Glu Thr Pro Phe Leu Leu Val Leu Ser Tyr Leu His
            275                 280                 285

Val His Thr Ala Leu Phe Ser Ser Lys Asp Phe Ala Gly Lys Ser Gln
290                 295                 300

His Gly Val Tyr Gly Asp Ala Val Glu Glu Met Asp Trp Ser Val Gly
305                 310                 315                 320

Gln Ile Leu Asn Leu Leu Asp Glu Leu Arg Leu Ala Asn Asp Thr Leu
                325                 330                 335

Ile Tyr Phe Thr Ser Asp Gln Gly Ala His Val Glu Glu Val Ser Ser
            340                 345                 350

Lys Gly Glu Ile His Gly Gly Ser Asn Gly Ile Tyr Lys Gly Gly Lys
            355                 360                 365

Ala Asn Asn Trp Glu Gly Gly Ile Arg Val Pro Gly Ile Leu Arg Trp
370                 375                 380

Pro Arg Val Ile Gln Ala Gly Gln Lys Ile Asp Glu Pro Thr Ser Asn
385                 390                 395                 400

Met Asp Ile Phe Pro Thr Val Ala Lys Leu Ala Gly Ala Pro Leu Pro
                405                 410                 415

Glu Asp Arg Ile Ile Asp Gly Arg Asp Leu Met Pro Leu Leu Glu Gly
            420                 425                 430

Lys Ser Gln Arg Ser Asp His Glu Phe Leu Phe His Tyr Cys Asn Ala
            435                 440                 445

Tyr Leu Asn Ala Val Arg Trp His Pro Gln Asn Ser Thr Ser Ile Trp
450                 455                 460

Lys Ala Phe Phe Phe Thr Pro Asn Phe Asn Pro Val Gly Ser Asn Gly
```

```
                465                 470                 475                 480
Cys Phe Ala Thr His Val Cys Phe Cys Phe Gly Ser Tyr Val Thr His
                    485                 490                 495

His Asp Pro Pro Leu Leu Phe Asp Ile Ser Lys Asp Pro Arg Glu Arg
            500                 505                 510

Asn Pro Leu Thr Pro Ala Ser Glu Pro Arg Phe Tyr Glu Ile Leu Lys
        515                 520                 525

Val Met Gln Glu Ala Ala Asp Arg His Thr Gln Thr Leu Pro Glu Val
    530                 535                 540

Pro Asp Gln Phe Ser Trp Asn Asn Phe Leu Trp Lys Pro Trp Leu Gln
545                 550                 555                 560

Leu Cys Cys Pro Ser Thr Gly Leu Ser Cys Gln Cys Asp Arg Glu Lys
                565                 570                 575

Gln Asp Lys Arg Leu Ser Arg
            580

<210> SEQ ID NO 2
<211> LENGTH: 2401
<212> TYPE: DNA
<213> ORGANISM: Homo sapiens
<220> FEATURE:
<221> NAME/KEY: CDS
<222> LOCATION: (204)..(1952)

<400> SEQUENCE: 2
gcctccagca gctgacggga cccagctgta gtgaggttgc agtgattgag taggattggc      60
ctgcttcaaa gcagaggttt ctcatgggaa tatgcttatt aaactcccac tggtgcagaa     120
accatgaaca gaggatgaac aagtgaagtt gcaatctcct ccatcacagc tcagttcccc     180
aacaacagga tcacaagctg gag atg cct tta agg aag atg aag atc cct ttc    233
                         Met Pro Leu Arg Lys Met Lys Ile Pro Phe
                           1               5                  10 ctc cta ctg ttc ttt ctg tgg gaa gcc gag agc cac gca gca tca agg      281
Leu Leu Leu Phe Phe Leu Trp Glu Ala Glu Ser His Ala Ala Ser Arg
             15                  20                  25 ccg aac atc atc ctg gtg atg gct gac gac ctc ggc att gga gat cct      329
Pro Asn Ile Ile Leu Val Met Ala Asp Asp Leu Gly Ile Gly Asp Pro
         30                  35                  40 ggg tgc tat ggg aac aaa act atc agg act ccc aat atc gac cgg ttg      377
Gly Cys Tyr Gly Asn Lys Thr Ile Arg Thr Pro Asn Ile Asp Arg Leu
     45                  50                  55 gcc agt ggg gga gtg aaa ctc act cag cac ctg gca gca tca ccg ctg      425
Ala Ser Gly Gly Val Lys Leu Thr Gln His Leu Ala Ala Ser Pro Leu
 60                  65                  70 tgc aca cca agc agg gca gcc ttc atg act ggc cgg tac cct gtc cga      473
Cys Thr Pro Ser Arg Ala Ala Phe Met Thr Gly Arg Tyr Pro Val Arg
 75                  80                  85                  90 tca gga atg gca tct tgg tcc cgc act gga gtt ttc ctc ttc aca gcc      521
Ser Gly Met Ala Ser Trp Ser Arg Thr Gly Val Phe Leu Phe Thr Ala
                 95                 100                 105 tct tcg gga gga ctt ccc acc gat gag att acc ttt gct aag ctt ctg      569
Ser Ser Gly Gly Leu Pro Thr Asp Glu Ile Thr Phe Ala Lys Leu Leu
            110                 115                 120 aag gat caa ggt tat tca aca gca ctg ata ggg aaa tgg cac ctt ggg      617
Lys Asp Gln Gly Tyr Ser Thr Ala Leu Ile Gly Lys Trp His Leu Gly
        125                 130                 135 atg agc tgt cac agc aag act gac ttc tgt cac cac cct tta cat cac      665
Met Ser Cys His Ser Lys Thr Asp Phe Cys His His Pro Leu His His
    140                 145                 150
```

```
ggc ttc aat tat ttc tat ggg atc tct ttg acc aat ctg aga gac tgc      713
Gly Phe Asn Tyr Phe Tyr Gly Ile Ser Leu Thr Asn Leu Arg Asp Cys
155             160                 165                 170 aag ccc gga gag ggc agt gtc ttc acc acg ggc ttc aag agg ctg gtc      761
Lys Pro Gly Glu Gly Ser Val Phe Thr Thr Gly Phe Lys Arg Leu Val
                175                 180                 185 ttc ctc ccc ctg cag atc gtc ggg gtc acc ctc ctt acc ctt gct gca      809
Phe Leu Pro Leu Gln Ile Val Gly Val Thr Leu Leu Thr Leu Ala Ala
            190                 195                 200 ctc aat tgt ctg ggg cta ctc cac gtg cct cta ggc gtt ttt ttc agc      857
Leu Asn Cys Leu Gly Leu Leu His Val Pro Leu Gly Val Phe Phe Ser
        205                 210                 215 ctt ctc ttc cta gca gcc cta atc ctg acc ctt ttc ttg ggc ttc ctt      905
Leu Leu Phe Leu Ala Ala Leu Ile Leu Thr Leu Phe Leu Gly Phe Leu
    220                 225                 230 cat tac ttc cgg ccc ctg aac tgc ttc atg atg agg aac tac gag atc      953
His Tyr Phe Arg Pro Leu Asn Cys Phe Met Met Arg Asn Tyr Glu Ile
235                 240                 245                 250 att cag cag ccc atg tcc tat gac aat ctc acc cag agg cta acg gtg     1001
Ile Gln Gln Pro Met Ser Tyr Asp Asn Leu Thr Gln Arg Leu Thr Val
                255                 260                 265 gag gcg gcc cag ttc ata cag cgg aac act gag act ccg ttc ctg ctt     1049
Glu Ala Ala Gln Phe Ile Gln Arg Asn Thr Glu Thr Pro Phe Leu Leu
            270                 275                 280 gtc ttg tcc tac ctc cac gtg cac aca gcc ctg ttc tcc agc aaa gac     1097
Val Leu Ser Tyr Leu His Val His Thr Ala Leu Phe Ser Ser Lys Asp
        285                 290                 295 ttt gct ggc aaa agt caa cac gga gtc tac ggg gat gct gtt gag gaa     1145
Phe Ala Gly Lys Ser Gln His Gly Val Tyr Gly Asp Ala Val Glu Glu
    300                 305                 310 atg gac tgg agt gtg ggg cag atc ttg aac ctt ctg gat gag ctg aga     1193
Met Asp Trp Ser Val Gly Gln Ile Leu Asn Leu Leu Asp Glu Leu Arg
315                 320                 325                 330 ttg gct aat gat acc ctc atc tac ttc aca tcg gac cag gga gca cat     1241
Leu Ala Asn Asp Thr Leu Ile Tyr Phe Thr Ser Asp Gln Gly Ala His
                335                 340                 345 gta gag gag gtg tct tcc aaa gga gaa att cat ggc gga agt aat ggg     1289
Val Glu Glu Val Ser Ser Lys Gly Glu Ile His Gly Gly Ser Asn Gly
            350                 355                 360 atc tat aaa gga gga aaa gca aac aac tgg gaa gga ggt atc cgg gtt     1337
Ile Tyr Lys Gly Gly Lys Ala Asn Asn Trp Glu Gly Gly Ile Arg Val
        365                 370                 375 cca ggc atc ctt cgt tgg ccc agg gtg ata cag gct ggc cag aag att     1385
Pro Gly Ile Leu Arg Trp Pro Arg Val Ile Gln Ala Gly Gln Lys Ile
    380                 385                 390 gat gag ccc act agc aac atg gac ata ttt cct aca gta gcc aag ctg     1433
Asp Glu Pro Thr Ser Asn Met Asp Ile Phe Pro Thr Val Ala Lys Leu
395                 400                 405                 410 gct gga gct ccc ttg cct gag gac agg atc att gat gga cgt gat ctg     1481
Ala Gly Ala Pro Leu Pro Glu Asp Arg Ile Ile Asp Gly Arg Asp Leu
                415                 420                 425 atg ccc ctg ctt gaa gga aaa agc caa cgc tcc gat cat gag ttt ctc     1529
Met Pro Leu Leu Glu Gly Lys Ser Gln Arg Ser Asp His Glu Phe Leu
            430                 435                 440 ttc cat tac tgc aac gcc tac tta aat gct gtg cgc tgg cac cct cag     1577
Phe His Tyr Cys Asn Ala Tyr Leu Asn Ala Val Arg Trp His Pro Gln
        445                 450                 455 aac agc aca tcc atc tgg aag gcc ttt ttc ttc acc ccc aac ttc aac     1625
Asn Ser Thr Ser Ile Trp Lys Ala Phe Phe Phe Thr Pro Asn Phe Asn
```

-continued

```
                460                     465                     470
ccc gtg ggt tcc aac gga tgc ttt gcc aca cac gtg tgc ttc tgt ttc      1673
Pro Val Gly Ser Asn Gly Cys Phe Ala Thr His Val Cys Phe Cys Phe
475                 480                 485                 490 ggg agt tat gtc acc cat cac gac cca cct tta ctc ttt gat att tcc      1721
Gly Ser Tyr Val Thr His His Asp Pro Pro Leu Leu Phe Asp Ile Ser
                495                 500                 505 aaa gat ccc aga gag aga aac cca cta act cca gca tcc gag ccc cgg      1769
Lys Asp Pro Arg Glu Arg Asn Pro Leu Thr Pro Ala Ser Glu Pro Arg
            510                 515                 520 ttt tat gaa atc ctc aaa gtc atg cag gaa gct gcg gac aga cac acc      1817
Phe Tyr Glu Ile Leu Lys Val Met Gln Glu Ala Ala Asp Arg His Thr
        525                 530                 535 cag acc ctg cca gag gtg ccc gat cag ttt tca tgg aac aac ttt ctt      1865
Gln Thr Leu Pro Glu Val Pro Asp Gln Phe Ser Trp Asn Asn Phe Leu
    540                 545                 550 tgg aag ccc tgg ctt cag ctg tgc tgt cct tcc acc ggc ctg tct tgc      1913
Trp Lys Pro Trp Leu Gln Leu Cys Cys Pro Ser Thr Gly Leu Ser Cys
555                 560                 565                 570 cag tgt gat aga gaa aaa cag gat aag aga ctg agc cgc tagcagcgcc      1962
Gln Cys Asp Arg Glu Lys Gln Asp Lys Arg Leu Ser Arg
                575                 580 tggggaccag acagacgcat gtggcaaagc tcaccatctt cactacaaac acgcctgaga    2022
gtggcactgg ggaaacataa ctccatctac accttggatt tggactgatt ctccatttta    2082
tcacctgaag gcttgggcca gagctcaaca gctactcaac tggaggggtg aggggataa     2142 ggtctgtagt atacagacag gaagatggta ggtttatgcc ttctgtggcc agagtcttgg    2202
actcatggaa atagaatgaa tagaggggca ttcacaaggc acaccagtgc aagcagatga    2262 caaaaggtg  cagaaggcaa tcttaaaaca gaaaggtgca ggaggtacct taactcaccc    2322
ctcagcaaat acctatgtca acagtataag ttaccattta ctctataatc tgcagtgatg    2382
caataaccag cataataaa                                                 2401
```